United States Patent
Shi et al.

(10) Patent No.: US 12,089,853 B2
(45) Date of Patent: Sep. 17, 2024

(54) MULTIPLE CLIP APPLIER

(71) Applicant: HANGZHOU SUNSTONE TECHNOLOGY CO., LTD., Hangzhou (CN)

(72) Inventors: Lei Shi, Hangzhou (CN); Wenjun Zhang, Hangzhou (CN); Weijian Dai, Hangzhou (CN); Yanli Ma, Hangzhou (CN)

(73) Assignee: HANGZHOU SUNSTONE TECHNOLOGY CO., LTD., Hangzhou (CN)

( * ) Notice: Subject to any disclaimer, the term of this patent is extended or adjusted under 35 U.S.C. 154(b) by 424 days.

(21) Appl. No.: 17/595,325

(22) PCT Filed: Apr. 10, 2020

(86) PCT No.: PCT/CN2020/084098
§ 371 (c)(1),
(2) Date: Nov. 15, 2021

(87) PCT Pub. No.: WO2020/238434
PCT Pub. Date: Dec. 3, 2020

(65) Prior Publication Data
US 2022/0211384 A1     Jul. 7, 2022

(30) Foreign Application Priority Data

May 24, 2019   (CN) .......................... 201910439205.2

(51) Int. Cl.
*A61B 17/128*     (2006.01)
*A61B 17/122*     (2006.01)
(Continued)

(52) U.S. Cl.
CPC ........ *A61B 17/1285* (2013.01); *A61B 17/122* (2013.01); *A61B 2017/0042* (2013.01); *A61B 2017/12004* (2013.01)

(58) Field of Classification Search
CPC .............. A61B 17/1285; A61B 17/122; A61B 2017/0042; A61B 2017/12004; A61B 2017/00407; A61B 2090/0807
See application file for complete search history.

(56) References Cited

U.S. PATENT DOCUMENTS

2002/0133178 A1     9/2002   Muramatsu et al.

FOREIGN PATENT DOCUMENTS

| CN | 101836882 A | 9/2010 |
| CN | 104490446 A | 4/2015 |

(Continued)

OTHER PUBLICATIONS

"International Application No. PCT/CN2020/084098, International Search Report and Written Opinion mailed May 27, 2020", (May 27, 2020), 13 pgs.

*Primary Examiner* — Brooke Labranche
(74) *Attorney, Agent, or Firm* — Schwegman Lundberg & Woessner, P.A.

(57) ABSTRACT

A multiple clip applier including a fixing handle, a conveying handle, a clamping handle, a pushing mechanism, a clip tube, a clip head and a closure clip assembly is provided. The clip head is arranged at one end of the clip tube, the clip tube is provided with a loading groove. The closure clip assembly is detachably arranged in the loading groove, and the clip tube includes an outer and an inner clip tube; the conveying handle and the clamping handle are both hinged with the fixing handle; and the clamping handle is linked with the outer clip tube to control opening or closing of the clip head. The closure clip assembly includes a plurality of closure clips; and the conveying handle is linked with the pushing (Continued)

mechanism to move along the length direction of the inner clip tube, thereby driving the closure clips to move towards the clip head.

11 Claims, 4 Drawing Sheets

(51) Int. Cl.
  *A61B 17/00* (2006.01)
  *A61B 17/12* (2006.01)

(56) References Cited

FOREIGN PATENT DOCUMENTS

| | | | | | |
|---|---|---|---|---|---|
| CN | 106214209 | A | | 12/2016 | |
| CN | 206612825 | U | | 11/2017 | |
| CN | 108577923 | A | * | 9/2018 | ......... A61B 17/1285 |
| CN | 207821868 | U | | 9/2018 | |
| CN | 110037765 | A | | 7/2019 | |
| WO | WO-2020238434 | A1 | | 12/2020 | |

* cited by examiner

MULTIPLE CLIP APPLIER

PRIORITY CLAIM TO RELATED APPLICATIONS

This application is a U.S. national stage filing under 35 U.S.C. § 371 from International Application No. PCT/CN2020/084098, filed on 10 Apr. 2020, and published as WO2020/238434 on 3 Dec. 2020, which claims the benefit under 35 U.S.C. 119 to Chinese Application No. 201910439205.2, filed on 24 May 2019, the benefit of priority of each of which is claimed herein, and which applications and publication are hereby incorporated herein by reference in their entirety.

TECHNICAL FIELD

The disclosure relates to a technical field of medical instruments, in particular to a multiple clip applier.

BACKGROUND ART

In a minimally invasive surgery, a closure clip is often used to clip lumen tissues such as human blood vessels, and the closure clip needs to be used in conjunction with a clip applier. At present, the clip applier used in conjunction with the closure clip is a one-shot type and only one closure clip can be clamped and installed at a time for the clip applier in surgical use. However, in all kinds of minimally invasive surgery, multiple lumen tissues need to be closed for many times. Therefore, the existing single-shot clip applier need to be installed several times and repeatedly enter and leave a human body surgical lumen for closing the clip applier. This frequent installation of the closure clip and its use in and out of the human body lumen increase risk of surgical infection of patients, increase operation time and probability of bleeding and leakage of lumen tissues, and greatly increase workload of medical personnel in instrument installation, use, cleaning and maintenance.

SUMMARY

In view of foregoing circumstances, a multiple clip applier is designed in this disclosure, which can be installed with different numbers of closure clip assemblies with different specifications according to requirements of various types of surgeries before a surgery so as to realize a function of multiple uses with one loading, and can close human lumen tissues at multiple sites quickly, conveniently and continuously, thereby reducing the risk of surgical infection of patients, greatly improving operation efficiency, improving the treatment timeliness and reducing workload of medical personnel.

Technical schemes adopted in the disclosure is as follows: a multiple clip applier is provided in this disclosure, which includes a fixing handle, a conveying handle, a clamping handle, a pushing mechanism, a clip tube, a clip head and a closure clip assembly. The fixing handle is provided with an installation cavity in which one end of the clip tube is arranged, the clip tube has a hollow structure and is communicated with the installation cavity, the clip head is arranged at the other end of the clip tube, and the clip tube is provided with a loading groove which is provided adjacent to the clip head. The closure clip assembly is detachably arranged in the loading groove, and the clip tube includes an outer clip tube and an inner clip tube both of which are of hollow structures; the outer clip tube is sleeved outside the inner clip tube, and the outer clip tube can move along a length direction of the inner clip tube; the conveying handle and the clamping handle are both hinged with the fixing handle; and the clamping handle is linked with the outer clip tube to control opening or closing of the clip head. The pushing mechanism is movably inserted into the inner clip tube, and the closure clip assembly includes a plurality of closure clips; and the conveying handle is linked with the pushing mechanism to move along the length direction of the inner clip tube, thereby driving the closure clips to move towards the clip head.

In an embodiment of the present disclosure, the multiple clip applier further includes a connecting rod, and the conveying handle is linked with the clamping handle through the connecting rod. When the conveying handle strikes and conveys the closure clip, the clamping handle is linked at the same time, so that a fixed clip head and a movable clip head are in a semi-closed state, for preventing the closure clip from popping off when being conveyed to the clip head.

In an embodiment of the present disclosure, the multiple clip applier further includes a rotating wheel and a rotating bearing. The rotating wheel is arranged at an end of the outer clip tube proximate to the fixing handle, and the rotating bearing is rotatably arranged in the installation cavity and at an end of the inner clip tube proximate to the fixing handle, and the outer clip tube and the inner clip tube are driven to rotate by rotating the rotating wheel, thereby driving the clip head to rotate with an angle of rotation 360°.

In an embodiment of the present disclosure, the multiple clip applier further includes a cleaning valve which passes through the rotating wheel and is communicated with the outer clip tube, and the inner clip tube is provided with a through slot hole, so that inside of the inner clip tube is communicated with outside of the multiple clip applier. The multiple clip applier also includes a protective cover which is detachably disposed on the cleaning valve and is made of silica gel.

In an embodiment of the present disclosure, the clip head includes a fixed clip head and a movable clip head, the fixed clip head is fixedly arranged on the inner clip tube, and the movable clip head is hinged with the inner clip tube and movably connected with the outer clip tube, and a brace bar is provided on the clamping handle, and the clamping handle is linked with the outer clip tube to move through the brace bar, thereby controlling opening or closing of the movable clip head relative to the fixed clip head.

In an embodiment of the present disclosure, the movable clip head is provided with a sliding groove and a blocking groove. The sliding groove inclines towards a connecting end of the movable clip head, and the blocking groove is proximate to a free end of the movable clip head for blocking the conveying and positioning of the closure clip and preventing the closure clip from falling off.

In an embodiment of the present disclosure, the conveying mechanism includes a stop bar, a push bar and a reset pull bar. One end of the push bar is arranged immediately opposite to the closure clip, the other end of the push bar is connected with the stop bar, a plurality of clamping teeth are arranged on the stop bar, and a conveying arm is provided on the conveying handle; the conveying arm is matched with a plurality of clamping teeth for driving the stop bar and the push bar to move towards the clip head; the reset pull bar is arranged on the stop bar; and the fixing handle is provided with a plurality of clamping grooves, and the reset pull bar is matched with the clamping grooves for the stopping of the stop bar.

In an embodiment of the present disclosure, the number of the clamping teeth is one more than the number of the closure clips, for enabling the loaded closure clip assembly to move towards the clip head by a closure clip pitch to be in a standby state.

In an embodiment of the present disclosure, a digital mark is provided on the stop bar, and a digital window is arranged at a position of the fixing handle corresponding to the digital mark, and a digit displayed in the digital window is a remaining number of the closure clips in the multiple clip applier.

In an embodiment of the present disclosure, the closure clip assembly further includes an upper suspension rail and a lower guide rail. The upper suspension rail and the lower guide rail are oppositely arranged; the closure clip is fixed by matching the upper suspension rail with the lower guide rail; and both the upper suspension rail and the lower guide rail are detachably arranged in the loading groove.

The disclosure has following beneficial effects: the multiple clip applier provided in this disclosure can be loaded with different numbers of closure clip assemblies with different specifications according to requirements of various types of surgeries before a surgery, and can close human lumen tissues quickly, conveniently and continuously, thereby reducing the risk of surgical infection of patients, greatly improving operation efficiency, improving the treatment timeliness and reducing workload of medical personnel.

In use, the closure clip assembly is pressed into the loading groove, and the closure clip in the loading groove is in a semi-closed state; then the conveying handle is gripped, and the conveying handle drives the pushing mechanism to move towards the clip head. At this time, the pushing mechanism pushes several closure clips to move towards the clip head in turn, and the clamping handle controls the clip head to open to be in a semi-closed state, and the closure clips can be guided into the clip head and this semi-closed state prevents the closure clips from falling off the clip head; then the clamping handle controls the clip head to be fully opened, and the closure clip is self-reset on the clip head to be in an open standby state; then, the clamping handle controls the clip head to close, so that the closure clip can clamp, mark or position lumen tissues such as human blood vessels.

Reference numbers in the figures are as follows: 1. Fixing Handle; 2. Conveying Handle; 3. Clamping Handle; 4. Pushing Mechanism; 5. Clip Tube; 6. Clip Head; 7. Closure Clip Assembly; 8. Connecting Rod; 9. Rotating Wheel; 10. Rotating Bearing; 12. Clamping Groove; 13. Digital Window; 51. Loading Groove; 71. Closure Clip; 72. Upper Suspension Rail; 73. Lower Guide Rail; 74. Disassembler; 52. Outer Clip Tube; 53. Inner Clip Tube; 91. Cleaning Valve; 531. Through Slot Hole; 61. Fixed Clip Head; 62. Movable Clip Head; 31. Brace Bar; 621. Sliding Groove; 622. Blocking Groove; 41. Stop Bar; 42. Push Bar; 43. Reset pull bar; 21. Conveying Arm; 411. Clamping Teeth; 412. Digital Mark; 711. Protrusion; 712. Upper Arm; 713. Lower Arm.

DETAILED DESCRIPTION

In the following, a detailed and complete description of the present disclosure will be made in combination with specific embodiments with reference to the drawings.

With reference to FIGS. 1-7, the present disclosure provides a multiple clip applier, which includes a fixing handle 1, a conveying handle 2, a clamping handle 3, a pushing mechanism 4, a clip tube 5, a clip head 6 and a closure clip assembly 7. The fixing handle 1 is provided with an installation cavity in which one end of the clip tube 5 is arranged, the clip tube 5 has a hollow structure and is communicated with the installation cavity, the clip head 6 is arranged at the other end of the clip tube 5, and the clip tube 5 is provided with a loading groove 51 which is provided adjacent to the clip head 6. The closure clip assembly 7 is detachably arranged in the loading groove 51, and the clip tube 5 includes an outer clip tube 52 and an inner clip tube 53 both of which are of hollow structures; the outer clip tube 52 is sleeved outside the inner clip tube 53, and the outer clip tube 52 can move along a length direction of the inner clip tube 53; the conveying handle 2 and the clamping handle 3 are both hinged with the fixing handle 1; and the clamping handle 3 is linked with the clip tube 5 to control opening or closing of the clip head 6. The pushing mechanism 4 is movably inserted into the inner clip tube 53 and the closure clip assembly 7 includes a plurality of closure clips 71; and the conveying handle 2 is linked with the pushing mechanism 4 to move along the length direction of the inner clip tube 53 thereby driving the closure clips 71 to move towards the clip head 6. The closure clip assembly 7 includes the plurality of closure clips 71, and different numbers of closure clip assemblies with different specifications can be selected and loaded according to requirements of various types of surgeries before a surgery, and can close human lumen tissues quickly, conveniently and continuously, thereby reducing the risk of surgical infection of patients, greatly improving operation efficiency, improving the treatment timeliness and reducing workload of medical personnel. In use, the closure clip assembly 7 is loaded into the loading groove 51, and the closure clip 71 in the loading groove 51 is in a semi-closed state; then the conveying handle 2 is gripped, and the conveying handle 2 drives the pushing mechanism 4 to move towards the clip head 6. At this time, the pushing mechanism 4 pushes several closure clips 71 to move towards the clip head 6 in turn, and the clamping handle 3 controls the clip head 6 to open to be in a semi-closed state, and the closure clips 71 can be guided into the clip head 6 and this semi-closed state prevents the closure clips 71 from falling off the clip head 6; then the clamping handle 3 controls the clip head 6 to be fully opened, and the closure clip 71 is self-reset on the clip head 6 to be in an open standby state; then, the clamping handle 3 controls the clip head 6 to close, so that the closure clip 71 can clip, mark or position lumen tissues such as human blood vessels.

Figure 1:
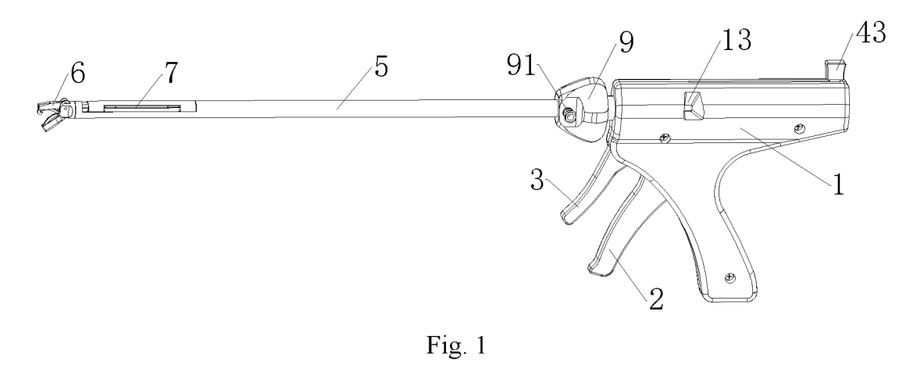
FIG. 1 is a schematic structural diagram of a multiple clip applier according to the present disclosure.
Figure 2:
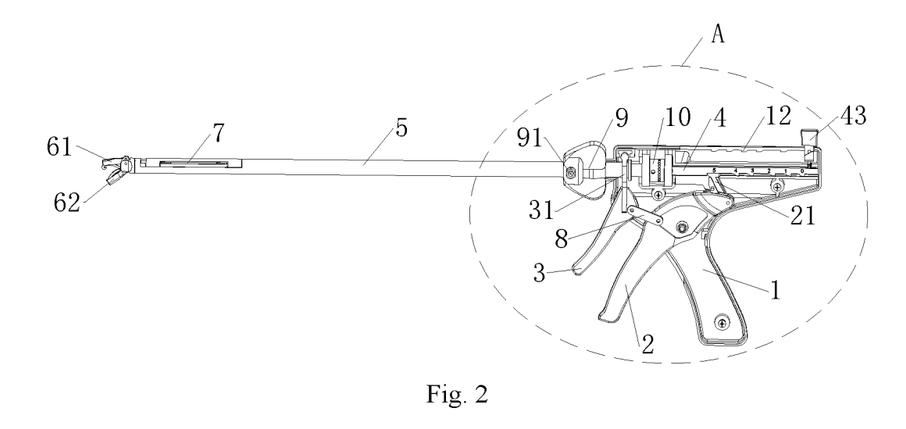
FIG. 2 is a schematic internal structural diagram of a multiple clip applier according to the present disclosure.

The multiple clip applier further includes a connecting rod 8, and the conveying handle 2 is linked with the clamping handle 3 through the connecting rod 8. When the conveying handle 2 strikes and conveys the closure clip 71, the clamping handle 3 is linked at the same time, so that the clip head 6 is in a semi-closed state, for preventing the closure clip 71 from popping off when being conveyed to the clip head 6. In use, since the conveying handle 2 and the clamping handle 3 are linked by the connecting rod 8, the clamping handle 3 can be driven to move when the conveying handle 2 gripped, and the clamping handle 3 synchronously move slightly with the clip head 62, so that the clip head 6 is in a semi-closed state, and a micro-movement of the clip head 6 can guide the closure clip 71 into the clip head 6, and the semi-closed state can prevent the closure clip 71 from falling off the clip head 6. The closure clip 71 is self-reset on the clip head 6 to be in an open standby state; then, the clamping handle 3 controls the clip head 6 to close, so that the closure clip 71 can clip lumen tissues such as human blood vessels.

Figure 3:
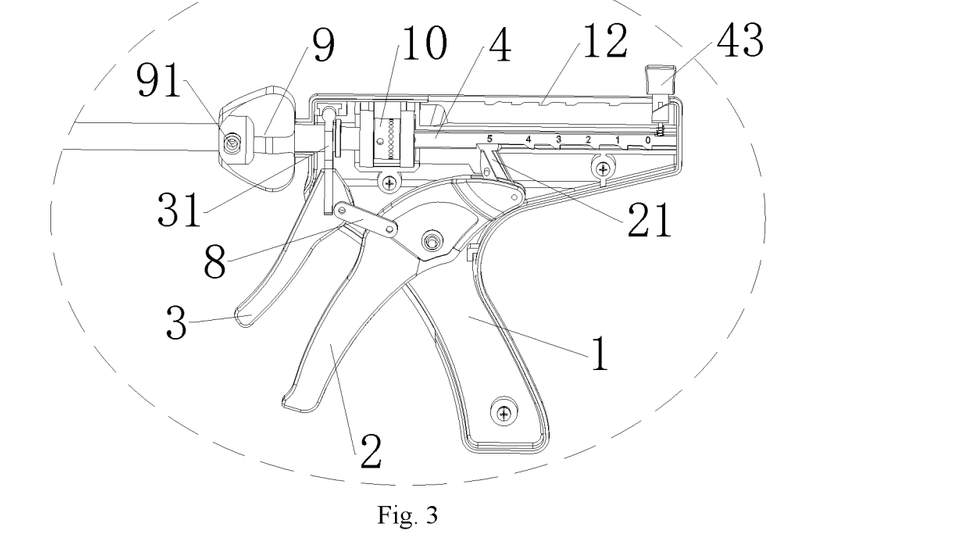
FIG. 3 is a partial enlarged view at A in FIG. 2.
Figure 4:
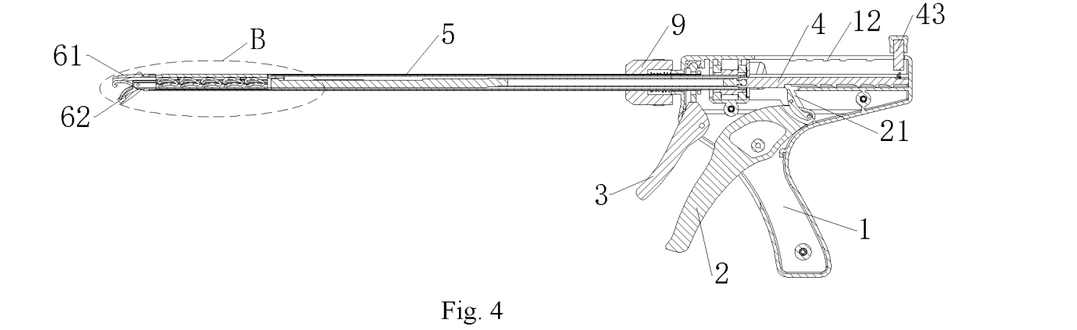
FIG. 4 is a schematic sectional diagram of a multiple clip applier according to the present disclosure.
Figure 5:
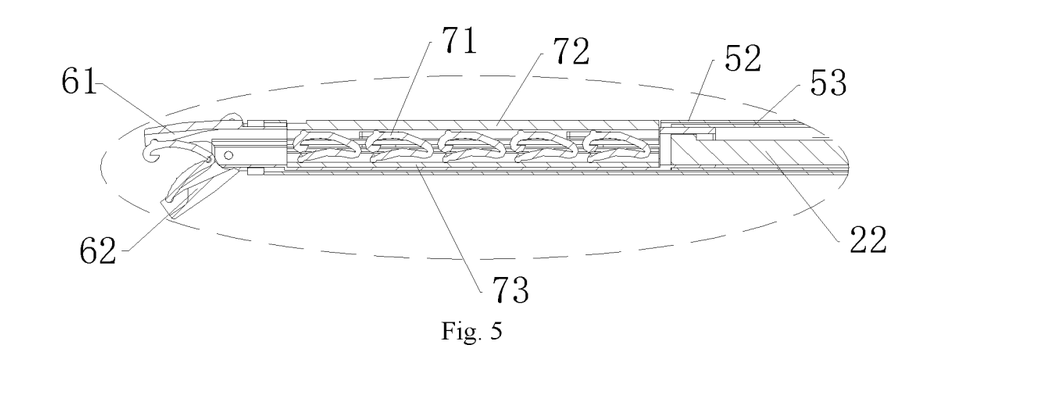
FIG. 5 is a partial enlarged view at B in FIG. 4.
Figure 6:
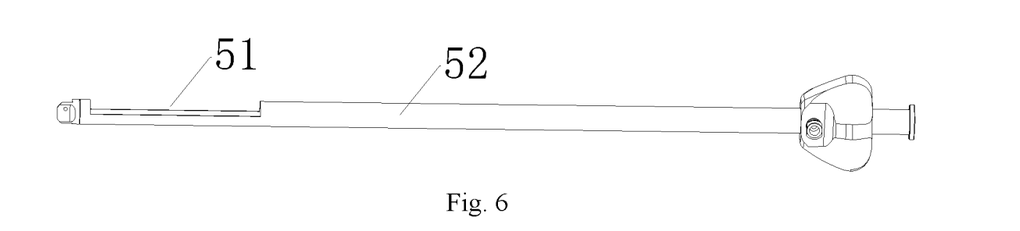
FIG. 6 is a schematic structural diagram of an outer clip tube according to the present disclosure.
Figure 7:
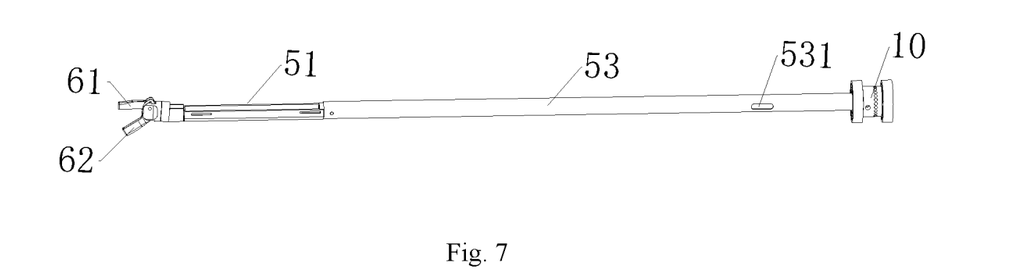
FIG. 7 is a schematic structural diagram of an inner clip tube according to the present disclosure.

As shown in FIGS. 2-3, the multiple clip applier further includes a rotating wheel 9 and a rotating bearing 10. The rotating wheel 9 is arranged at an end of the outer clip tube 52 proximate to the fixing handle 1, and the rotating bearing 10 is rotatably arranged in the installation cavity and at an end of the inner clip tube proximate to the fixing handle 1, and the outer clip tube 52 and the inner clip tube 53 are driven to rotate by rotating the rotating wheel 9, thereby driving the clip head 62 to rotate with a rotation angle of 360°. The rotating wheel 9 controls rotation of the outer clip tube 52 and the inner clip tube 53 to drive the rotating bearing 10 at an end of the inner clip tube 53 to rotate, thus realizing a whole rotation of the clip tube 5, causing the clip head 6 and the closure clip assembly 7 at an end of the clip tube 5 to rotate, thus realizing a function of adjusting an opening direction of the clip head 6 at a treatment site. Preferably, the rotation angle is 360 degrees, and an adjustment range of the direction of the clip head 6 is wide. The wheel 9 can be provided with a plurality of ribs, and in this way friction between a hand and the rotating wheel 9 can be increased, and the hand is not easy to slip, which is convenient for applying a force.

As shown in FIG. 1, the multiple clip applier also includes a cleaning valve 91, which passes through the rotating wheel 9 and is connected with the outer clip tube 52. The inner clip tube 53 is provided with a through slot hole 531, and the inner clip tube 53 communicates with the outer clip tube 52 through the through slot hole 531, which can maintain internal and external communication when the outer clip tube 52 moves in the length direction, thus facilitating cleaning. During cleaning, it is only necessary to directly flushing the cleaning valve 91, and there is no need to disassemble and reassemble during cleaning and disinfection, which reduces the workload and skill requirements of medical personnel, and also avoids damage, missing, mixed assembly and wrong assembly of parts due to frequent disassembly, assembly, cleaning and disinfection.

The multiple clip applier also comprises a protective cover which is detachably arranged on the cleaning valve 91, and the protective cover is made of silica gel, which is soft and has good sealing performance.

As shown in FIGS. 2-3, the clip head 6 includes a fixed clip head 61 and a movable clip head 62. The fixed clip head 61 is fixed on the inner clip tube 53, the movable clip head 62 is hinged with the inner clip tube 53 and movably connected with the outer clip tube 52. The clamping handle 3 is provided with a brace bar 31, and the clamping handle 3 is linked with the outer clip tube 52 to move through the brace bar 31, thereby controlling opening or closing of the movable clip head 62 relative to the fixed clip head 61.

In operation, the conveying handle 2 is gripped and released, so that the closure clip 71 enters the clip head 6 in a semi-closed state and then unfolds, and is kept in a guide rail between the fixed clip head 61 and the movable clip head 62 for later use. After reaching the treatment site, the lumen tissue to be clipped is placed in an inner space of the closure clip 71, and a hooked upper arm 712 of the closure clip 71 is used to confirm whether the lumen tissue is within a closable range of the closure clip 71. After confirmation, an appropriate force is applied to the clamping handle 3 to limit moving of the lumen tissue. Finally, the clamping handle 3 is pulled to lock the upper arm 712 and the lower arm 713 of the closure clip 71 and clip the lumen tissue, then the clamping handle 3 is released, the outer clip tube 52 is reset, the fixed clip head 61 and the movable clip head 62 are opened, so that the closure clip 71 clipped on the lumen tissue is detached from the clip head 6, and the clipping operation of the closure clip 71 is completed.

Figure 9:
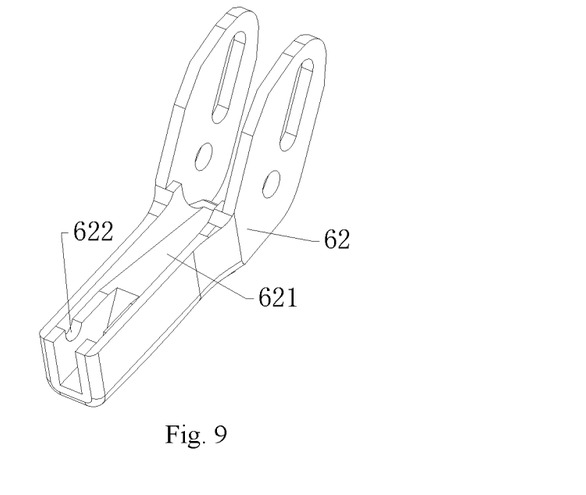
FIG. 9 is a schematic structural diagram of a movable clip head according to the present disclosure.
Figure 11:
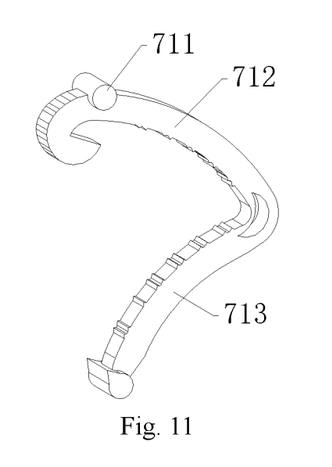
FIG. 11 is a schematic structural diagram of a closure clip according to the present disclosure.

As shown in FIG. 9 and FIG. 11, the movable clip head 62 is provided with a sliding groove 621 and a blocking groove 622. The sliding groove 621 inclines towards a connecting end of the movable clip head 62, and the blocking groove 622 is proximate to a free end of the movable clip head 62 for preventing the closure clip 71 from falling off. The closure clip 71 is pushed by the pushing mechanism 4 to reach the clip head 6, and the sliding groove 621 of the movable clip head 62 guides the closure clip 71 and stops it with the blocking groove 622. The closure clip 71 is provided with a protrusion 711 which is clamped on the blocking groove 622 for stopping. The closure clip 71 includes an upper arm 712 and a lower arm 713, and a number of the protrusions 711 is two. The two protrusions 711 are respectively arranged on force application points of the upper arm 712 and the lower arm 713, so that the clip head 6 facilitates opening and clipping the closure clip 71.

Figure 8:
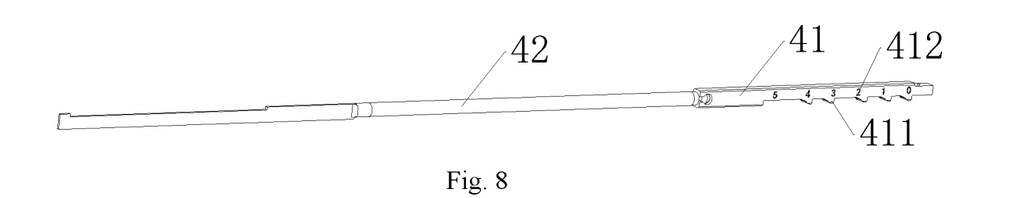
FIG. 8 is a schematic structural diagram of a pushing mechanism according to the present disclosure.

As shown in FIG. 2 and FIG. 8, the conveying mechanism includes a stop bar 41, a push bar 42 and a reset pull bar 43. One of the push bar 42 is arranged immediately opposite to the closure clip 71, the other end of the push bar 42 is connected with the stop bar 41, a plurality of clamping teeth 411 are arranged on the stop bar 41, and a conveying arm 21 is provided on the conveying handle 2; the conveying arm 21 is matched with a plurality of clamping teeth 411 for driving the stop bar 41 and the push bar 42 to move towards the clip head 6; the reset pull bar 43 is arranged on the stop bar 41; and the fixing handle 1 is provided with a plurality of clamping grooves 12, and the reset pull bar 43 is matched with the clamping grooves 12 for the stopping of the stop bar 41. Each time the conveying handle 2 is gripped, the closure clips 71 in semi-closed state arranged in sequence are pulled by the stop bar 41 and push bar 42 to move towards the clip head 6 by a distance of the closure clips 71, and the reset pull bar 43 connected to the stop bar 41 moves towards the clip head 6 at the same time and is clamped in the clamping groove 12 to stop the stop bar 41. When replacing the closure clip assembly 7, by pressing the reset pull bar 43 and controlling the stop bar 41 to move in a direction away from the clip head 6, the push bar 42 is driven to return to an original position and get out of a range of the closure clip assembly 7, which facilitates installation and replacement of the closure clip assembly 7.

Figure 10:
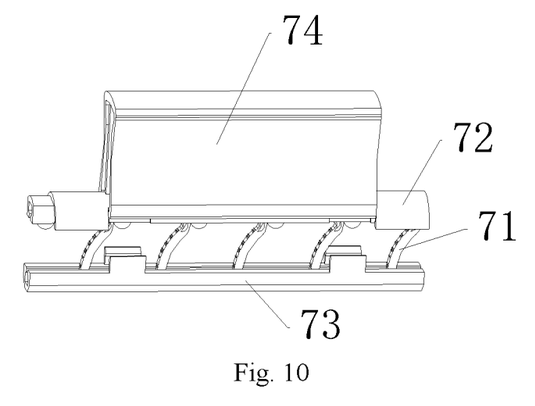
FIG. 10 is a schematic structural diagram of a closure clip assembly according to the present disclosure.

The number of the teeth 411 is one more than the number of the closure clips 71. After the closure clip assembly 7 is installed, the conveying handle 2 needs to be pulled twice before the first closure clip 71 at the forefront of the closure clip assembly 7 can be conveyed to the clip head 6. Because the clip head 6 is of a precise moving structure, in order to prevent the clip head 6 from being deformed due to a pressure for overlapping the upper suspension rail 72 and the lower guide rail 73 in installing the closed clamp assembly 7, an empty space of the closed clamp 71 is reserved between the loading groove 51 and the clip head 6, which can ensure tightness of the clip applier. When using a second closure clip 71, one closure clip 71 can be conveyed to the clip head 6 by pulling the conveying handle 2 once.

As shown in FIG. 1 and FIG. 8, a digital mark 412 is provided on the stop bar 41, and a digital window 13 is arranged at a position of the fixing handle 1 corresponding to the digital mark 412, and a remaining number of the closure clips 71 in the clip applier can be observed through the digital window 13 for timely replacement.

As shown in FIG. 10, the closure clip assembly 7 further includes an upper suspension rail 72 and a lower guide rail 73. The upper suspension rail 72 and the lower guide rail 73 are oppositely arranged; the closure clip 71 is fixed by matching the upper suspension rail 72 with the lower guide rail 73; and both the upper suspension rail 72 and the lower guide rail 73 are detachably arranged in the loading groove. In a factory state, the closure clip assembly 7 has been pre-installed with different types and quantities of closure clips 71. Compared with the single loading method, a loading efficiency is greatly improved, the workload and skill requirements of medical personnel are reduced, and a failure risk due to multiple loadings is also reduced. Preferably, the closure clip assembly 7 is further provided with a disassembler 74 which is detachably connected with the upper suspension rail 72, and with the disassembler 74 provided, the hand will not directly contact with and pollute the closure clip 71.

The above is only preferred embodiments of the present disclosure, which does not limit a protection scope of the present disclosure. Any equivalent transformation made with the specification of the present disclosure, which is directly or indirectly applied to other related technical fields, is included within the scope of the disclosure.

What is claimed is:

1. A multiple clip applier, comprising:
a fixing handle, a conveying handle, a clamping handle, a pushing mechanism, a clip tube, a clip head and a closure clip assembly, wherein the fixing handle is provided with an installation cavity, one end of the clip tube is arranged in the installation cavity, the clip tube has a hollow structure and is communicated with the installation cavity, the clip head is arranged at an another end of the clip tube, and the clip tube is provided with a loading groove which is provided adjacent to the clip head; the closure clip assembly is detachably arranged in the loading groove, and the clip tube comprises an outer clip tube and an inner clip tube both of which are of hollow structures; the outer clip tube is sleeved outside the inner clip tube, and the outer clip tube moves along a length direction of the inner clip tube; the conveying handle and the clamping handle are both hinged with the fixing handle; and the clamping handle is linked with the outer clip tube to control opening or closing of the clip head; the pushing mechanism is movably inserted into the inner clip tube, and the closure clip assembly comprises a plurality of closure clips; and the conveying handle is linked with the pushing mechanism to move along the length direction of the inner clip tube, thereby driving the closure clips to move towards the clip head;
wherein the multiple clip applier further comprises a rotating wheel and a rotating bearing, the rotating wheel is arranged at an end of the outer clip tube proximate to the fixing handle, and the rotating bearing is rotatably arranged in the installation cavity and at an end of the inner clip tube proximate to the fixing handle, and the outer clip tube and the inner clip tube are driven to rotate by rotating the rotating wheel, thereby driving the clip head to rotate with an angle of rotation of 360°.

2. The multiple clip applier according to claim 1, wherein the multiple clip applier further comprises a connecting rod, wherein the conveying handle and the clamping handle are linked through the connecting rod.

3. The multiple clip applier according to claim 1, wherein the multiple clip applier further comprises a cleaning valve, wherein the cleaning valve passes through the rotating wheel and is communicated with the outer clip tube, and the inner clip tube is provided with a through slot hole, so that inside of the inner clip tube is communicated with outside of the multiple clip applier through the cleaning valve; the multiple clip applier also comprises a protective cover which is detachably disposed on the cleaning valve and the protective cover is made of silica gel.

4. The multiple clip applier according to claim 1, wherein the clip head comprises a fixed clip head and a movable clip head, the fixed clip head is fixedly arranged on the inner clip tube, and the movable clip head is hinged with the inner clip tube and movably connected with the outer clip tube; and a brace bar is provided at the clamping handle, and the clamping handle is linked with the outer clip tube to move through the brace bar, thereby controlling opening or closing of the movable clip head relative to the fixed clip head.

5. The multiple clip applier according to claim 4, wherein the movable clip head is provided with a sliding groove and a blocking groove, the sliding groove inclines towards a connecting end of the movable clip head and the blocking groove is proximate to a free end of the movable clip head for blocking conveying and positioning of the closure clips and preventing the closure clips from falling off.

6. The multiple clip applier according to claim 5, wherein at least one closure clip is provided with a protrusion, the protrusion is clamped on the blocking groove for stopping; the at least one closure clip comprises an upper arm and a lower arm, one closure clip has at least two protrusions, and the two protrusions of the same closure clip are respectively arranged on force application points of the upper arm and the lower arm, so that the clip head facilitates opening and clipping the closure clip.

7. The multiple clip applier according to claim 1, wherein the conveying mechanism comprises a stop bar, a push bar and a reset pull bar, one end of the push bar is arranged immediately opposite to the closure clip, an another of the push bar is connected with the stop bar, a plurality of clamping teeth are arranged at the stop bar, and a conveying arm is provided at the conveying handle; the conveying arm is matched with a plurality of clamping teeth for driving the stop bar and the push bar to move towards the clip head; the reset pull bar is arranged on the stop bar; and the fixing handle is provided with a plurality of clamping grooves, and the reset pull bar is matched with the clamping grooves for the stopping of the stop bar.

8. The multiple clip applier according to claim 7, wherein a number of the clamping teeth is one more than a number of the closure clips.

9. The multiple clip applier according to claim 7, wherein a digital mark is provided on the stop bar, and a digital window is provided at a position of the fixing handle corresponding to the digital mark.

10. The multiple clip applier according to claim 1, wherein the closure clip assembly further comprises an upper suspension rail and a lower guide rail, wherein the upper suspension rail and the lower guide rail are oppositely arranged, the closure clips are fixed by matching the upper suspension rail with the lower guide rail, and both the upper suspension rail and the lower guide rail are detachably arranged in the loading groove.

11. The multiple clip applier according to claim 10, wherein the closure clip assembly is provided with a disassembler, and the disassembler is detachably connected with the upper suspension rail.

* * * * *